United States Patent
Snell

[11] Patent Number: 5,954,666
[45] Date of Patent: Sep. 21, 1999

[54] SYSTEM FOR ANALYZING SPECIFIC PORTIONS OF CARDIAC WAVEFORMS

[75] Inventor: Jeffery D. Snell, Oak Park, Calif.

[73] Assignee: Pacesetter, Inc., Sylmar, Calif.

[21] Appl. No.: 08/511,566

[22] Filed: Aug. 4, 1995

[51] Int. Cl.⁶ .................................................. A61B 5/044
[52] U.S. Cl. ........................................... 600/523; 607/32
[58] Field of Search ............................. 128/696, 697, 128/700, 704, 709, 710; 364/413.05, 413.06; 607/32; 600/509, 510, 513, 517, 522, 523

[56] References Cited

U.S. PATENT DOCUMENTS

| | | |
|---|---|---|
| 3,782,367 | 1/1974 | Hochberg et al. . |
| 3,898,984 | 8/1975 | Mandel et al. . |
| 4,098,267 | 7/1978 | Stein et al. . |
| 4,142,533 | 3/1979 | Brownlee et al. . |
| 4,193,393 | 3/1980 | Schlager .................................. 128/710 |
| 4,374,382 | 2/1983 | Markowitz ......................... 340/870.01 |
| 4,476,869 | 10/1984 | Bihn . |
| 4,527,567 | 7/1985 | Fischler et al. . |
| 4,596,255 | 6/1986 | Snell et al. .............................. 128/697 |
| 4,791,936 | 12/1988 | Snell et al. .............................. 128/697 |
| 4,809,697 | 3/1989 | Causey, III et al. . |
| 4,825,869 | 5/1989 | Sasmor et al. . |
| 4,989,610 | 2/1991 | Patton et al. ............................ 128/695 |
| 5,092,341 | 3/1992 | Kelen ...................................... 128/702 |
| 5,224,486 | 7/1993 | Lerman et al. ......................... 128/696 |
| 5,284,152 | 2/1994 | Portnuff et al. ........................ 128/710 |
| 5,305,202 | 4/1994 | Gallant et al. ..................... 364/413.06 |
| 5,402,794 | 4/1995 | Wahlstrand et al. ................... 128/696 |
| 5,425,373 | 6/1995 | Causey, III ............................. 128/697 |
| 5,447,164 | 9/1995 | Shaya et al. ............................ 128/710 |

*Primary Examiner*—Jeffrey R. Jastrzab

[57] ABSTRACT

A system for analyzing cardiac waveforms is provided that allows a physician to accurately measure specific portions of a displayed IEGM or EKG signal. By examining the cardiac waveform with the analyzing system, the physician can quickly and accurately determine whether the device is operating properly. The physician may use one or two cursors or an icon or pointer to define a specific portion of the cardiac waveform to be analyzed. Various waveform characteristics such as relative waveform amplitude, maximum slew rate, power spectral density, and time elapsed can be determined for the specific portion of the cardiac waveform. If desired, the waveform characteristic determined for the specific portion of the cardiac waveform can be compared to statistical waveform data (e.g., in the form of a histogram).

49 Claims, 2 Drawing Sheets

SYSTEM FOR ANALYZING SPECIFIC PORTIONS OF CARDIAC WAVEFORMS

BACKGROUND OF THE INVENTION

This invention relates to systems for analyzing cardiac data, and more particularly to systems for analyzing specific portions of cardiac waveforms to determine how to optimize the programming of cardiac stimulating devices to best serve a patient's needs.

Implantable cardiac stimulating devices, such as pacemakers, are well known. Fairly sophisticated devices are presently available that apply electrical pulses to a patient's heart in response to various measured cardiac events. Because each patient has a different cardiac condition, many cardiac stimulating devices are provided with programmable settings which govern their operation. A physician can tailor a cardiac stimulating device to a patient's individual needs by adjusting these settings using a "programmer," as described in commonly-assigned U.S. Pat. No. 4,809,697 to Causey, III et al.

Some of the programmable settings are detection criteria, which the cardiac stimulating device uses to identify cardiac events. For example, a cardiac stimulating device that measures a patient's internal heartbeat signal—known as the ventricular intracardiac electrogram (IEGM)—may determine which regions of the IEGM signal correspond to R-waves based on a comparison of the measured signal to several programmable detection criteria, including a predetermined amplitude threshold. Unless an R-wave has an amplitude greater than the threshold, it will not be detected by the cardiac stimulating device.

In order to ensure that the detection criteria are set properly, a physician can simultaneously monitor the operation of a patient's cardiac stimulating device and the patient's IEGM. The measured IEGM is generally transmitted to a programmer by the cardiac stimulating device via telemetry. The programmer can be used to display both the IEGM data and various other information such as a patient's electrocardiogram (EKG) on a display monitor or chart recorder. Event markers, such as the letter "R" to represent a detected R-wave, can also be displayed adjacent to the region of the IEGM signal that corresponds to the event. Markers are generated by the cardiac stimulating device whenever a cardiac event is detected.

Analysis of the patient's cardiac rhythm using markers can be used to establish if other operating parameters of the cardiac stimulating device are set optimally. Markers are generated when cardiac events are detected by the cardiac stimulating device, such as P-waves for atrial depolarization and R-waves for ventricular depolarization. In addition, the cardiac stimulating device may generate markers to signal significant timing events, such as the end of a refractory period or minimum tracking interval. If desired, the markers can be used in conjunction with IEGM and EKG signals, for example, to establish if the refractory period should be shorter, to sense a faster atrial rate, or longer, to avoid retrograde atrial events.

An apparatus for displaying event markers adjacent to an IEGM signal is described in commonly-assigned U.S. Pat. No. 4,791,936 to Snell et: al. Such an apparatus can be useful in aiding a physician to determine whether the various cardiac stimulating device settings are adjusted properly. For example, the physician can examine the IEGM and EKG signals and make a judgement as to whether the event markers displayed adjacent to various cardiac events appear to be appropriate and whether the operation of the device seems to be correct.

Nevertheless, even if the physician suspects that the cardiac stimulating device is not operating optimally, the cause of the problem may be unclear. For example, the physician might suspect that a particular cardiac event has not been correctly identified by the cardiac stimulating device because the amplitude of a particular corresponding cardiac signal fell below the threshold level programmed into the device. However, an accurate determination of the magnitude of the cardiac signal in a specific portion of the cardiac waveform generally necessitates a careful measurement of the displayed signal, typically using calipers or some other mechanical measurement instrument. Physical measurement of the displayed cardiac signal on the display monitor or chart recorder output is slow, may be cumbersome, and may introduce undesirable measurement errors.

In an effort to alleviate some of the difficulties associated with physically measuring the cardiac data, systems of the type described in the aforementioned U.S. Pat. No. 4,791, 936 to Snell et al. have been developed that display certain supplemental data, such as the time that has elapsed between R-waves or other cardiac events. However, frequently data is required that is related to an event that the cardiac stimulating device did not identify properly. If the cardiac stimulating device fails to identify the necessary cardiac event, such as an R-wave, then it is generally not possible to provide supplemental data related to that event. It would therefore be desirable for the physician to be able analyze specific portions of IEGM or EKG waveforms more rapidly and more completely, which would allow the physician to adjust the settings of a cardiac stimulating device more accurately.

SUMMARY OF THE INVENTION

In accordance with the principles of the present invention, a system for analyzing cardiac waveforms is provided that allows a physician to accurately measure specific portions of a displayed IEGM or EKG waveform without mechanical measurement instruments. By analyzing specific portions of the cardiac waveform with this system, the physician can quickly and accurately determine whether a cardiac stimulating device is operating properly. For example, if a physician suspects that a specific portion of the cardiac waveform corresponding to a cardiac event has not been correctly identified by a cardiac stimulating device, the analyzing system can be used to determine the desired waveform characteristic (amplitude, slew rate, power spectral density, time elapsed, etc.) of that specific portion of the cardiac waveform. This additional information can be used by the physician to help evaluate whether the detection criteria for the device are adjusted properly.

In one embodiment, the physician may use a pair of cursors to define the specific portion of the cardiac waveform to be analyzed to determine the desired waveform characteristic. For example, the two cursors can be used to specify two points on a waveform so that the analyzing system can determine the time elapsed between these two points. After the physician positions the cursors in their desired locations, the analyzing system calculates the desired waveform characteristic of the specific portion of the waveform defined by the cursors and displays the result on a display unit.

If desired, a single cursor or pointer can be used to define the specific portion of the cardiac waveform to be analyzed. After the physician positions the single cursor in the desired position, the analyzing system calculates, for example, the amplitude of the cardiac signal in the portion of the waveform immediately adjacent to the single cursor and displays the result on the display unit.

In a preferred embodiment, the physician invokes measurement routines that are represented by icons on the display. When a measurement routine is invoked, the system analyzes the portion of the cardiac waveform immediately adjacent to the icon in order to calculate the desired waveform characteristic, such as maximum amplitude, maximum slew rate, power spectral density, or time elapsed.

Thus, unlike conventional systems for analyzing and displaying cardiac waveforms, the physician can select the specific portion of the cardiac waveform that is to be analyzed to determine various waveform characteristics. The specific region can be defined using the two-cursor, single-cursor/pointer, or icon arrangement.

The analyzing system also analyzes entire waveform record files. For example, the analyzing system can scan a waveform for cardiac waveform artifacts, such as R-waves, and automatically attach corresponding labelling icons to each R-wave. Alternatively, the system can automatically place cursors on a waveform at detected R-wave minimums and maximums. Following the initial placement, the physician can reposition the labelling icons or cursors. If desired, the physician can also add or remove the cursors or the icons.

In addition, the analyzing system allows the physician to compare the waveform characteristics (e.g. amplitude, slew rate, time elapsed, power spectral density, etc.) of specific portions of the cardiac waveform to statistical waveform data. Either a numerical or graphical display can be used.

For example, the measured amplitude of an R-wave in a selected portion of the waveform can be displayed in a histogram of R-wave amplitudes to place the measured amplitude in context. The R-wave amplitudes in the histogram can be measured in real-time, either at a time prior to making the measurements that are currently being analyzed, or concurrently, while the analyzing system is being used to analyze a specific portion of a cardiac waveform.

The R-wave amplitudes for the histogram can also be retrieved from a stored histogram file. If desired, the R-wave amplitudes in the histogram can represent R-wave amplitudes compiled from measurements of many separate patients (and therefore be representative of a segment or cross-section of the general population) or can correspond to the measured amplitudes of a single patent. By displaying a measured waveform characteristic from a specific portion of the waveform in the context of a statistical distribution of such characteristics, the physician using the analyzing system can more readily diagnose a patient's condition. For example, by displaying a measured R-wave amplitude from a specific portion of the waveform in the context of a histogram of previously measured R-wave amplitudes, the physician can better asses whether such an R-wave is likely to recur.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which.

DETAILED DESCRIPTION OF THE PREFERRED EMBODIMENT

Figure 1:
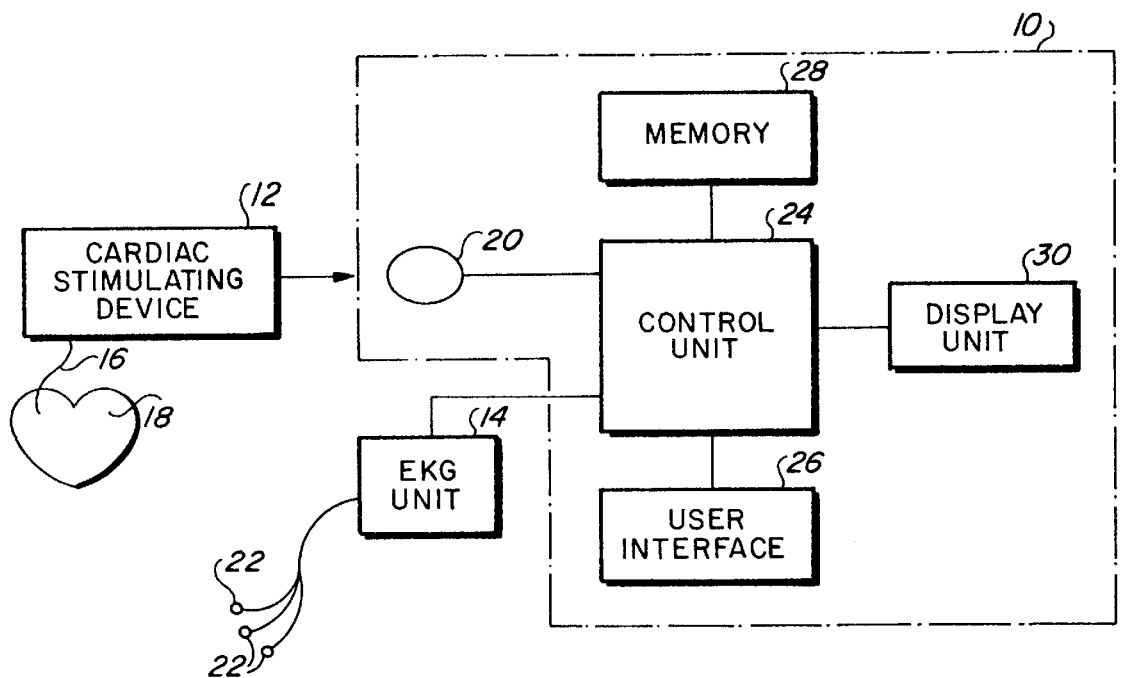
FIG. 1 is a schematic diagram showing a system for analyzing cardiac waveforms in accordance with the present invention.

A system for analyzing cardiac waveforms in accordance with the present invention is shown in FIG. 1. An analyzing system 10 receives cardiac signals from a cardiac stimulating device 12 and cardiac monitoring device such as an EKG unit 14. The cardiac stimulating device 12, which is implanted in a patient (not shown), measures the patient's IEGM signal typically via a suitable electrical conductor such as a lead 16, which is connected to the patient's heart 18. The IEGM signal and event markers generated by the cardiac stimulating device 12 may be transmitted to the analyzing system 10 via telemetry. The analyzing system 10 can receive the transmitted data via a telemetry head 20. If it is desired to analyze EKG data, the analyzing system 10 can process EKG data that is acquired using the EKG unit 14, which is connected to the patient using surface electrodes 22.

The analyzing system 10 contains a control unit 24, which receives commands from a user such as a physician (not shown) via a user interface 26 The user interface 26 may be any convenient user-friendly input interface such as a keyboard, mouse, trackball, or pen. If desired, the user interface 26 can be merged with a display terminal in the form of a touch screen. The control unit 24 processes the user commands, the cardiac data received from the cardiac stimulating device 12, and cardiac data from the EKG unit 14. Cardiac data may be stored by the control unit 24 in memory 28. Preferably, the control unit 24 contains a microprocessor and other logic circuitry for implementing the instructions received from the user.

Figure 2:
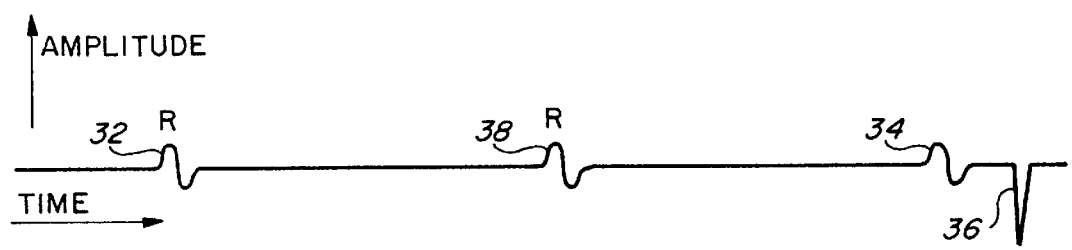
FIG. 2 is a representation of a cardiac waveform as it appears on the display unit of the analyzing system in accordance with the present invention.

The IEGM and EKG signals and corresponding event markers can be displayed on a display unit 30. FIG. 2 shows a representative IEGM signal that is measured by the cardiac stimulating device 12 (FIG. 1). When the cardiac stimulating device 12 (FIG. 1) identifies a cardiac event, such as an R-wave, an event marker is generally transmitted by the cardiac stimulating device 12 to the analyzing system 10. An event marker symbol 32, such as the letter "R" representing a confirmed R-wave, may be displayed on the display unit 30 (FIG. 1) adjacent to the identified cardiac event.

However, if a cardiac event occurs that is not identified by the cardiac stimulating device 12 (FIG. 1), an event marker is not generated and the cardiac waveform on the display unit 30 (FIG. 1) is therefore typically not labeled. For example, as shown in FIG. 2, if an R-wave 34 is not identified by the cardiac stimulating device 12 (FIG. 1), then the letter "R" is not displayed adjacent to the portion of the cardiac waveform that corresponds to that R-wave.

FIG. 2 also illustrates another consequence of the failure of the cardiac stimulating device 12 (FIG. 1) to identify the R-wave 34. If no R-wave is identified, the cardiac stimulating device 12 applies a pacing pulse 36 to the patient's heart 18 (FIG. 1). When the base pacing rate is 60 pulses per minute, the pacing pulse 36 is applied one second after the last confirmed R-wave 38. The pacing pulse 36 is applied to ensure that the patient's heart rate does not drop below a predefined minimum rate. However, because the physician can observe that an R-wave in fact occurred, it will be apparent that the cardiac stimulating device 12 (FIG. 1) is not functioning as desired.

Because the R-wave 34 has a lower amplitude than a preceding R-wave 38, the physician may suspect that the R-wave threshold for the cardiac stimulating device 12 (FIG. 1) has been set too high and that the R-wave 34 was not identified because it did not exceed the threshold level. With a conventional apparatus, as discussed above, the physician would generally have been forced to physically measure the waveform recorded on the chart to determine the amplitude, slew rate, or time elapsed between two specific points. For example, to determine whether the amplitude of an R-wave exceeds the R-wave threshold, physicians have generally needed to measure the height of the waveform on the chart, calculate the waveform amplitude, and compare the calculated amplitude to the programmed threshold setting. Determining more complex waveform characteristics, such as the power spectral density of a specific portion of the waveform (e.g. by performing a Fourier transform analysis of a portion of the cardiac waveform), has not been possible.

Accurate measurements of various waveform characteristics other than waveform amplitude are also desirable. Measurement of an R-wave amplitude alone may not necessarily allow a physician to establish the reason that an R-wave was not identified, because the measured amplitude of the R-wave is affected by the frequency content of the R-wave. Cardiac monitoring devices such as the EKG unit 14 (FIG. 1) and cardiac stimulating devices 12 (FIG. 1) generally have filter circuitry, such as bandpass filters, to reduce spurious noise and make the cardiac stimulating devices 12 (FIG. 1) more selective with respect to signals with the frequency signature of a cardiac R-wave. Because such bandpass filters affect R-waves with varying frequency contents differently, the physician cannot readily discern the effective amplitude of the R-wave without establishing the frequency content of the R-wave. The traditional approach has been to measure the slew rate of the cardiac signal, by measuring either the slope of a line from a minimum point to a maximum point in the R-wave, or by establishing the maximum slope of the R-wave based on visually identifying the steepest tangent line to the R-wave waveform. These measurement techniques are inexact and it has not been practical to use more accurate methods, such as the well-known Fourier transform analysis technique, because the IEGM waveform has been in printed form.

In accordance with the present invention, the physician can use the analyzing system 10 of FIG. 1 to analyze a specific portion of the cardiac waveform by interacting directly with data presented on the display. During the initial display of IEGM and EKG data, the control unit 24 stores these cardiac waveforms in the memory 28. For long-term storage of relatively large quantities of cardiac data the memory 28 contains a non-volatile silicon memory, a hard disk drive, a magnetic tape unit or an optical storage device. Volatile memory devices such as random access memory (RAM) are contained within the memory 28 for temporary storage of cardiac data and for storage of instructions which direct operation of the control unit 24. In order to analyze a specific portion of a cardiac waveform, the relevant portion of the cardiac data stored in the memory 28 is retrieved and displayed on the display unit 30. Preferably, cardiac data is stored in the memory 28 in the form of individual files, which can be organized using standard database techniques. The relevant portion of a file may be accessed by any convenient method, such as by manually panning through the file after it has been retrieved or using the control unit 24 to analyze the file to locate any apparent cardiac irregularities.

Figure 3:
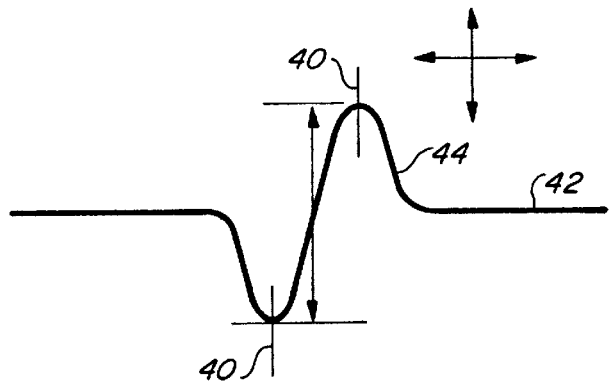
FIG. 3 is a representation of a cardiac waveform showing the use of cursors to measure waveform amplitude in accordance with the present invention.

Cursors can be used to define the specific portion of the cardiac waveform to be analyzed. For example, as shown in FIG. 3, a pair of cursors; 40 can be used to make an amplitude measurement of the specific portion of the cardiac waveform corresponding to a waveform segment 42. A physician can also use the cursors to measure the time elapsed between points on the waveform segment 42. The cursors 40 are positioned by entering commands via the user interface 26. If the user interface 26 is a keyboard, the physician can use directional keys to position the cursors 40. If the user interface 26 is a mouse, a pointer can be used, either to move the cursors 40, or to position one or more pointers. If a digitizing pen is used, the cursors 40 can be manipulated directly. The cursors 40 can be moved in tandem, or either cursor can be moved independently.

After positioning the cursors (pointers) on the display to define the specific portion of the cardiac waveform to be analyzed, the physician can instruct the control unit 24 (FIG. 1) to calculate the amplitude, maximum slew-rate, time elapsed, or power spectral density in the specific portion defined by the cursors 40. If a cardiac waveform such a; that shown in FIG. 2 is observed, for example, the physician can position the cursors 40 at the minimum and maximum points on an R-wave complex 44 as shown in FIG. 3. The control unit 24 (FIG. 1) calculates the relative amplitude for the selected specific portion of the cardiac waveform by determining the distance between the cursors 40. Alternatively, within the specific portion of the cardiac waveform, a single cursor or a pointer can be used to indicate a point at which the amplitude of the waveform is to be calculated. If a single cursor is used, the relative signal amplitude is determined by automatically finding the local minimum and maximum points of the R-wave on either side of the cursor. After calculating the waveform amplitude, the control unit 24 (FIG. 1) displays this waveform characteristic on the display unit 30 (FIG. 1). Using the control unit 24 (FIG. 1) of the analyzing system 10 (FIG. 1) to calculate the amplitude of the R-wave 34 (FIG. 2), it can be quickly determined if the reason that the cardiac stimulating device 12 (FIG. 1) applied the pacing pulse 36 (FIG. 2) was that the cardiac stimulating device 12 (FIG. 1) did not properly identify the R-wave 34 (FIG. 2) because the R-wave threshold amplitude was too low.

One factor that affects the measured amplitude of cardiac waveforms is the frequency content of the waveform, because cardiac stimulating devices 12 (FIG. 1) generally have frequency-dependent filter circuitry, such as a bandpass filter, to reduce spurious noise in the measured cardiac signals. Typically, such filters have a pass band that covers the frequency range of signals normally encountered by the cardiac stimulating devices 12 (FIG. 1). Cardiac signals with unusually high or low frequencies will be attenuated, which causes the bandpass filter to affect R-waves with varying frequency components differently. If desired, the physician may analyze the frequency content of an R-wave by using the control unit 24 (FIG. 1) to measure the slew rate of the R-wave or to calculate a power spectral density, e.g. by Fourier transform of the specific portion of the cardiac waveform corresponding to the R-wave signal. To analyze the frequency content of this specific portion of the cardiac waveform, the physician can position the cursors 50, such as those shown in FIG. 5, to define the specific portion of the waveform to analyze. The control unit 24 (FIG. 1) can calculate the slew rate or Fourier transform of the portion of the waveform between the cursors 50 (FIG. 5) or a specific portion of the waveform that is immediately adjacent to the single cursor using conventional signal processing techniques. To define the point at which a single slew rate measurement is made within the specific portion of the cardiac waveform to be analyzed, the physician can position a single cursor (e.g., one of cursors 50 in FIG. 5) at the appropriate point, allowing the control unit 24 (FIG. 1) to calculate the slew rate at that point.

It is possible that the R-wave 34 shown in FIG. 2 was not identified by the cardiac stimulating device 12 (FIG. 1) because the R-wave 34 occurred too soon after the R-wave 38. In order to avoid sensing R-waves twice and to avoid improperly identifying T-waves as R-waves, cardiac stimulating devices generally do not attempt to identify cardiac events for a time known as the refractory period following each identified R-wave. If the cardiac stimulating device 12 (FIG. 1) is programmed to have an excessively long refractory period, R-waves may occur within the refractory period which will not be identified by the device. With a conventional apparatus it is only possible to automatically calculate the time elapsed between those R-waves that are properly identified. In contrast, with the analyzing system 10 (FIG. 1) of the present invention, a physician can manually position the cursors 40 precisely where desired on the R-wave 38 and the R-wave 34, respectively, in order to define a specific portion of the cardiac waveform and thus determine the time between these two events (FIG. 2). The physician can therefore accurately determine whether the cardiac stimulating device failed to identify the R-wave 34 because the refractory period was too long.

Figure 4:
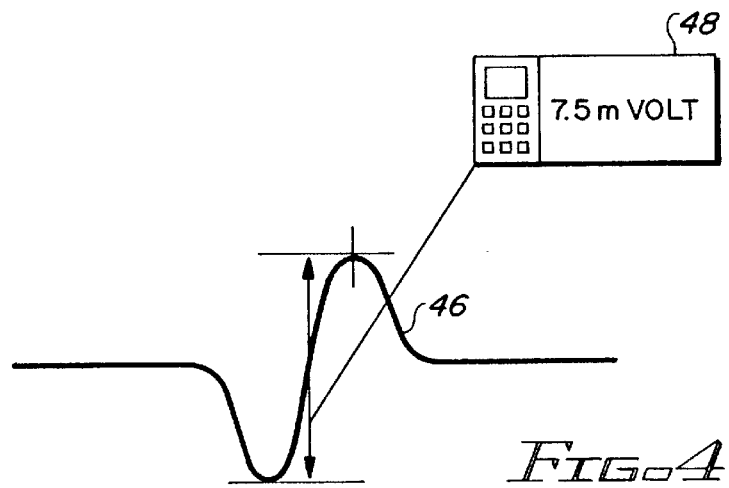
FIG. 4 is a representation of a cardiac waveform showing the use of an icon to measure waveform amplitude in accordance with the present invention.

In addition to defining the specific portions of the cardiac waveform to be analyzed using one or more cursors, the physician can invoke measurement routines represented by icons on the display unit 30 (FIG. 1). For example, if it is desired to measure the amplitude of a cardiac complex within a specific portion of a cardiac waveform, a physician can invoke an amplitude measurement routine by positioning a voltmeter icon 48 (FIG. 4) adjacent to the complex. If the voltmeter icon 48 is placed adjacent to the peak of an R-wave, as shown in FIG. 4, the control unit 24 (FIG. 1) will calculate the amplitude of an R-wave 46 by retrieving the cardiac waveform data corresponding to the desired specific portion of the cardiac waveform (the portion of the waveform immediately adjacent to the icon) and determining the maximum and minimum values of the signal within that specific portion of the waveform. The result of the amplitude calculation may be displayed next to the voltmeter icon 48. Similarly, measurement routines and corresponding icons can be used to determine other waveform characteristics such as slew rate, time elapsed, power spectral density etc.

The extent of the waveform that is defined as being "immediately adjacent" to an icon (and which therefore corresponds to the specific portion of the waveform to be analyzed) is preferably preset for each type of waveform characteristic to be determined. For example, if an amplitude measurement is to be made, the maximum relative amplitude (the local maximum minus the local minimum amplitude) of the cardiac waveform within a range of approximately +/−50.0 ms from the icon (or single cursor) position will be returned. Similarly, if a measurement routine is invoked to measure the slew rate of the cardiac signal, the maximum slew rate within a range of approximately +/−50.0 ms can be calculated. A larger range of approximately 2000 ms can be used if an icon is used to invoke cardiac cycle timing measurements, R-wave to R-wave, for example. If desired, the physician can modify the ranges that the measurement routines use.

If the user interface 26 shown in FIG. 1 is a keyboard, icons can be positioned using directional keys. If the user interface 26 is a mouse, it may be preferable to position the icons by "dragging" them across the screen of the display unit 30 with the mouse pointer. Other approaches for instructing the control unit 24 to invoke routines are also possible, such as using a pen or touch screen for user interface 26, with which the physician may select an icon and the desired position of the icon.

Figure 5:
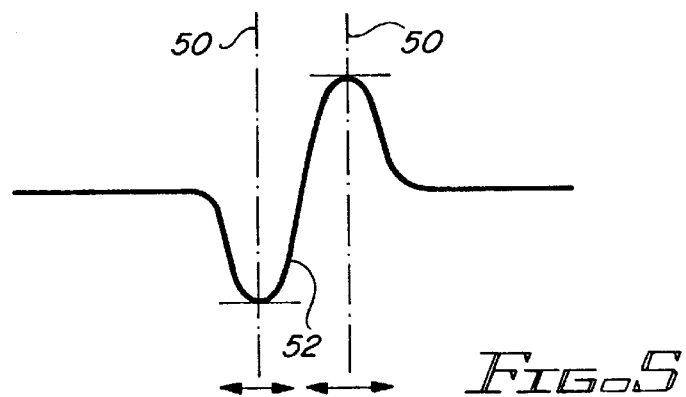
FIG. 5 is a representation of a cardiac waveform showing the use of cursors to measure waveform slew rate in accordance with the present invention.

Although an icon such as the voltmeter icon 48 may be desirable, it is not necessary to use icons to invoke analysis routines. Depending on the type of user interface 26 that is used, it may be preferable to invoke analysis of a specific portion of the cardiac waveform by using cursors, a pointer, or by encircling the specific portion of the waveform that is of interest using a pen or mouse. For example, one of the cardiac stimulating device detection criteria is the measured slew rate of the cardiac signal. As shown in FIG. 5, a pair of cursors 50 can be positioned to select a specific portion of the cardiac waveform 52 for slew rate analysis. After the physician positions the cursors 50 and invokes the slew rate routine, the control unit 24 (FIG. 1) calculates and displays the maximum value of the slope of the tangent to the waveform between the cursors 50, which is the maximum slew rate in that specific portion of the waveform.

The control unit 24 shown in FIG. 1 can also analyze an entire waveform record file. For example, the control unit 24 can scan the waveform for cardiac waveform artifacts, such as R-waves. The control unit 24 can then automatically attach icons, such as the voltmeter icon 48 (FIG. 4), to each R-wave. Alternatively, the control unit 24 can position the cursors 40 (FIG. 3) on the waveform at, for example, R-wave minimums and maximums that are identified by the control unit 24. Following the initial placement of the icons such as voltmeter icon 48 (FIG. 4) or the cursors 40 (FIG. 3) by the control unit 24, the user has an opportunity to reposition the icons or cursors. If desired, the user can also add or remove the cursors 40 (FIG. 3) or the icons such as voltmeter icon 48 (FIG. 4).

Figure 6:
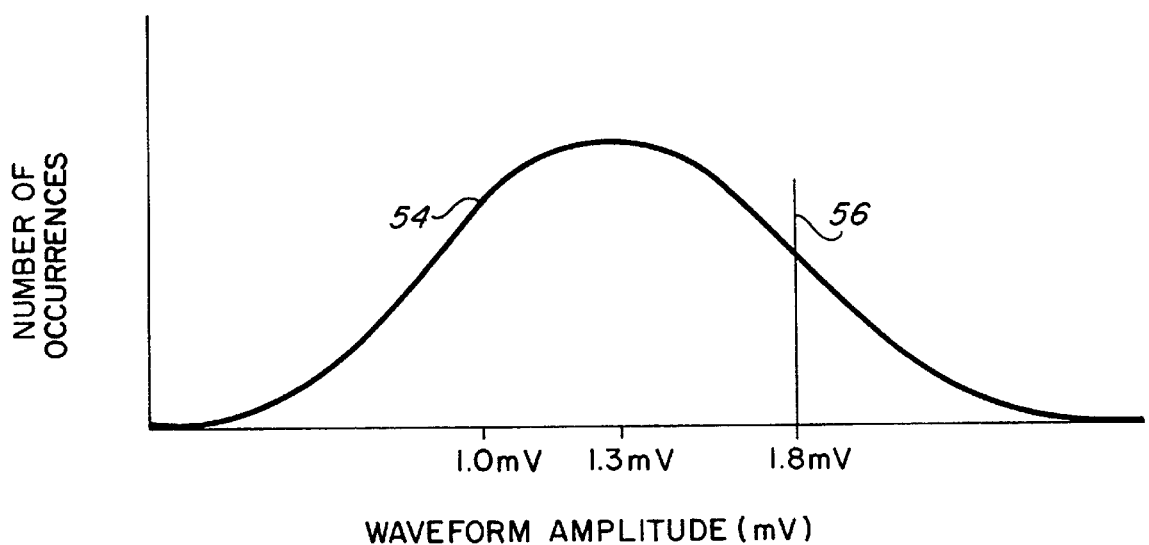
FIG. 6 is an illustrative histogram showing the number of measured waveforms with various amplitudes. Also shown is a line representing a recently measured waveform amplitude.

In addition, with the control unit 24 of FIG. 1, the physician can use the analyzing system 10 to compare desired waveform characteristics (e.g. amplitude, slew rate, etc.) for specific portions of the cardiac waveform to statistical waveform data. Either a numerical or graphical display can be used. For example, as shown in FIG. 6, the measured amplitude of an R-wave within a specific portion of the cardiac waveform can be displayed in a histogram of R-wave amplitudes to place the measured amplitude in context. The histogram curve 54 represents the number of R-waves with various amplitudes. The line 56 corresponds to the amplitude of the specific portion of the cardiac waveform selected by the physician for analysis.

The R-wave amplitudes that make up the histogram curve 54 can be measured in real-time either at a time prior to making the measurements that are currently being analyzed by the physician or can be accumulated concurrently, while the analyzing system is being used to analyze specific portions of the cardiac waveform. The R-wave amplitudes for the histogram can also be retrieved from a stored histogram file.

If desired, the R-wave amplitudes in the histogram can correspond to the measured R-waves of a particular patient. The histogram can also represent R-wave amplitudes compiled from measurements of many separate patients. Such a compilation can be representative of a specific segment of the population or a general cross-section of the population. Similar histograms can be used for any desired waveform characteristic.

By displaying a measured waveform characteristic for a specific portion of the cardiac waveform in the context of a statistical distribution of such characteristics, the physician using the analyzing system 10 can more readily diagnose a patient's condition. For example, by displaying a measured R-wave amplitude in the context of a histogram of previously measured R-wave amplitudes, the physician can asses whether such an R-wave is likely to recur.

One skilled in the art will appreciate that the present invention can be practiced by other than the described embodiments, which are presented for the purposes of illustration and not of limitation, and the present invention is limited only by the claims that follow.

What is claimed is:

1. A system for analyzing specific portions of cardiac waveforms using a measurement routine, comprising:
   a control unit;
   a display unit on which a cardiac waveform is displayed;
   memory in which the cardiac waveform is stored; and
   a user interface connected to the control unit for receiving instructions from a user and for providing these instructions to the control unit, such that the user can use the control unit to:
      define a specific portion of the cardiac waveform to be analyzed to determine a desired waveform characteristic;
      invoke the measurement routine to analyze the specific portion;
      analyze the specific portion of the cardiac waveform with the measurement routine to determine the desired waveform characteristic; and
      display the desired waveform characteristic on the display unit.

2. The system of claim 1 further comprising a telemetry head for receiving the cardiac waveform from an implanted cardiac stimulating device.

3. The system of claim 1 further comprising means for receiving the cardiac waveform from an electrocardiogram unit which can be attached to a patient with surface electrodes.

4. A system for analyzing specific portions of cardiac waveforms using a measurement routine, comprising;
   a control unit;
   a display unit on which a cardiac waveform is displayed;
   memory in which the cardiac waveform is stored; and
   user interface connected to the control unit for receiving instructions from a user and for providing these instructions to the control unit, such that the user can use the control unit to:
      define a specific portion of the cardiac waveform to be analyzed to determine a desired waveform characteristic;
      invoke the measurement routine to analyze the specific portion;
      analyze the specific portion of the cardiac waveform with the measurement routine to determine the desired waveform characteristic; and
      display the desired waveform characteristic on the display unit, wherein the control unit comprises means for generating at least one cursor on the display unit that may be positioned by the user by entering instructions via the user interface, the cursor defining the specific portion of the cardiac waveform to be analyzed as being the portion of the waveform immediately adjacent to the cursor.

5. The system of claim 4, wherein the control unit further comprises means for calculating the cardiac waveform relative amplitude within the specific portion of the cardiac waveform to be analyzed.

6. The system of claim 4, wherein the control unit further comprises means for calculating the maximum slew rate of the cardiac waveform within the specific portion of the cardiac waveform to be analyzed.

7. The system of claim 4, wherein the control unit further comprises means for calculating the power spectral density of the cardiac waveform within the specific portion of the cardiac waveform to be analyzed.

8. A system for analyzing specific portions of cardiac waveforms using a measurement routine, comprising:
   a control unit;
   a display unit on which a cardiac waveform is displayed;
   memory in which the cardiac waveform is stored; and
   a user interface connected to the control unit for receiving instructions from a user and for providing these instructions to the control unit, such that the user can use the control unit to:
      define a specific portion of the cardiac waveform to be analyzed to determine a desired waveform characteristic;
      invoke the measurement routine to analyze the specific portion;
      analyze the specific portion of the cardiac waveform with the measurement routine to determine the desired waveform characteristic; and
      display the desired waveform characteristic on the display unit, wherein the control unit comprises means for generating at least two cursors on the display unit that may be positioned by the user by entering instructions via the user interface, the cursors defining the specific portion of the cardiac waveform to be analyzed as being the portion of the waveform between the cursors.

9. The system of claim 8, wherein the control unit further comprises means for calculating the cardiac waveform relative amplitude within the specific portion of the cardiac waveform to be analyzed.

10. The system of claim 8, wherein the control unit further comprises means for calculating the maximum slew rate of the cardiac waveform within the specific portion of the cardiac waveform to be analyzed.

11. The system of claim 8, wherein the control unit further comprises means for calculating the power spectral density of the cardiac waveform within the specific portion of the cardiac waveform to be analyzed.

12. The system of claim 8, wherein the two cursors define an elapsed time to be measured by the control unit.

13. A system for analyzing specific portions of cardiac waveforms using a measurement routine, comprising:
   a control unit;
   a display unit on which a cardiac waveform is displayed;
   memory in which the cardiac waveform is stored; and
   a user interface connected to the control unit for receiving instructions from a user and for providing these instructions to the control unit, such that the user can use the control unit to:

define a specific portion of the cardiac waveform to be analyzed to determine a desired waveform characteristic;

invoke the measurement routine to analyze the specific portion;

analyze the specific portion of the cardiac waveform with the measurement routine to determine the desired waveform characteristic; and display the desired waveform characteristic on the display unit, wherein the control unit comprises means for generating icons on the display unit that may be positioned by the user to define the specific portion of the cardiac waveform to be analyzed.

14. The system of claim 13, wherein the control unit further comprises means for calculating the cardiac waveform relative amplitude within the specific portion of the cardiac waveform to be analyzed.

15. The system of claim 13, wherein the control unit further comprises means for calculating the maximum slew rate of the cardiac waveform within the specific portion of the cardiac waveform to be analyzed.

16. The system of claim 13, wherein the control unit further comprises means for calculating the power spectral density of the cardiac waveform within the specific portion of the cardiac waveform to be analyzed.

17. A system for analyzing specific portions of cardiac waveforms using a measurement routine, comprising:

a control unit;

a display unit on which a cardiac waveform is displayed;

memory in which the cardiac waveform is stored; and a user interface connected to the control unit for receiving instructions from a user and for providing these instructions to the control unit, such that the user can use the control unit to:

define a specific portion of the cardiac waveform to be analyzed to determine a desired waveform characteristic;

invoke the measurement routine to analyze the specific portion;

analyze the specific portion of the cardiac waveform with the measurement routine to determine the desired waveform characteristic; and display the desired waveform characteristic on the display unit; and means for comparing the desired waveform characteristic for the specific portion of the cardiac waveform to statistical waveform data.

18. A method for analyzing specific portions of cardiac waveforms with a measurement routine using a system having a control unit, a display, memory, and a user interface comprising the steps of:

receiving a cardiac waveform with the system;

displaying the cardiac waveform on the display unit;

storing the cardiac waveform in the memory; and receiving instructions from a user via the user interface and, with the control unit and in response to the instructions:

defining a specific portion of the cardiac waveform to be analyzed to determine a desired waveform characteristic;

invoking the measurement routine to analyze the specific portion;

analyzing the specific portion of the cardiac waveform with the measurement routine to determine the desired waveform characteristic; and displaying the desired waveform characteristic on the display unit.

19. The method of claim 18, wherein the step of receiving the cardiac waveform further comprises the step of receiving the cardiac waveform from a cardiac stimulating device with a telemetry head.

20. The method of claim 18, wherein the step of receiving the cardiac waveform further comprises the step of receiving the cardiac waveform from an electrocardiogram unit which is attached to a patient with surface electrodes.

21. A method for analyzing specific portions of cardiac waveforms with a measurement routine using a system having a control unit, a display, memory, and a user interface, comprising the steps of:

receiving a cardiac waveform with the system;

displaying the cardiac waveform on the display unit;

storing the cardiac waveform in the memory; and receiving instructions from a user via the user interface and, with the control unit and in response to the instructions:

defining a specific portion of the cardiac waveform to be analyzed to determine a desired waveform characteristic;

invoking the measurement routine to analyze the specific portion;

analyzing the specific portion of the cardiac waveform with the measurement routine to determine the desired waveform characteristic; and displaying the desired waveform characteristic on the display unit; and generating at least one cursor on the display unit that may be positioned by the user, the cursor defining the specific portion of the cardiac waveform to be analyzed as being the portion of the waveform immediately adjacent to the cursor.

22. The method of claim 21, wherein the step of analyzing comprises the step of measuring the relative amplitude of the specific portion of the cardiac waveform.

23. The method of claim 21, wherein the step of analyzing comprises the step of measuring the maximum slew rate of the specific portion of the cardiac waveform.

24. The method of claim 21, wherein the step of analyzing comprises the step of measuring the power spectral density of the specific portion of the cardiac waveform.

25. A method for analyzing specific portions of cardiac waveforms with a measurement routine using a system having a control unit, a display, memory, and a user interface, comprising the steps of:

receiving a cardiac waveform with the system;

displaying the cardiac waveform on the display unit;

storing the cardiac waveform in the memory; and receiving instructions from a user via the user interface and, with the control unit and in response to the instructions:

defining a specific portion of the cardiac waveform to be analyzed to determine a desired waveform characteristic;

invoking the measurement routine to analyze the specific portion;

analyzing the specific portion of the cardiac waveform with the measurement routine to determine the desired waveform characteristic; and displaying the desired waveform characteristic on the display unit; and generating two cursors on the display unit that may be positioned by the user to define the specific portion of the cardiac waveform to be analyzed.

26. The method of claim 25, wherein the step of analyzing comprises the step of measuring the relative amplitude of the specific portion of the cardiac waveform.

27. The method of claim 25, wherein the step of analyzing comprises the step of measuring the maximum slew rate of the specific portion of the cardiac waveform.

28. The method of claim 25, wherein the step of analyzing comprises the step of measuring the power spectral density of the specific portion of the cardiac waveform.

29. The method of claim 25, wherein the two cursors define an elapsed time to be measured by the control unit.

30. A method for analyzing specific portions of cardiac waveforms with a measurement routine using a system having a control unit, a display, memory, and a user interface, comprising the steps of:
   receiving a cardiac waveform with the system;
   displaying the cardiac waveform on the display unit;
   storing the cardiac waveform in the memory; and
   receiving instructions from a user via the user interface and, with the control unit and in response to the instructions:
      defining a specific portion of the cardiac waveform to be analyzed to determine a desired waveform characteristic;
      invoking the measurement routine to analyze the specific portion;
      analyzing the specific portion of the cardiac waveform with the measurement routine to determine the desired waveform characteristic; and
      displaying the desired waveform characteristic on the display unit; and
   generating an icon on the display unit that may be positioned by the user to define the specific portion of the cardiac waveform to be analyzed.

31. The method of claim 30, wherein the step of analyzing comprises the step of measuring the relative amplitude of the specific portion of the cardiac waveform.

32. The method of claim 30, wherein the step of analyzing comprises the step of measuring the maximum slew rate of the specific portion of the cardiac waveform.

33. The method of claim 30, wherein the step of analyzing comprises the step of measuring the power spectral density of the specific portion of the cardiac waveform.

34. A method for analyzing specific portions of cardiac waveforms with a measurement routine using a system having a control unit, a display, memory, and a user interface, comprising the steps of:
   receiving a cardiac waveform with the system;
   displaying the cardiac waveform on the display unit;
   storing the cardiac waveform in the memory; and
   receiving instructions from a user via the user interface and, with the control unit and in response to the instructions:
      defining a specific portion of the cardiac waveform to be analyzed to determine a desired waveform characteristic;
      invoking the measurement routine to analyze the specific portion;
      analyzing the specific portion of the cardiac waveform with the measurement routine to determine the desired waveform characteristic; and
      displaying the desired waveform characteristic on the display unit, wherein the step of displaying the desired waveform characteristic comprises the step of comparing the desired waveform characteristic for the specific portion of the cardiac waveform to statistical waveform data.

35. A programmer for programming cardiac stimulating devices and for analyzing specific portions of intracardiac electrogram waveforms, comprising:
   means for programming the cardiac stimulating devices;
   a control unit;
   a telemetry head for receiving an intracardiac electrogram waveform from one of the cardiac stimulating devices for analysis by the control unit;
   a display unit on which the intracardiac electrogram waveform is displayed;
   memory in which the intracardiac electrogram waveform is stored; and
   a user interface connected to the control unit for receiving instructions from a user and providing these instructions to the control unit, such that the user can use the control unit to:
      define a specific portion of the intracardiac electrogram waveform to be analyzed to determine a desired waveform characteristic;
      invoke the measurement routine to analyze the specific portion;
      analyze the specific portion of the intracardiac electrogram waveform with the measurement routine to determine the desired waveform characteristic; and
      display the desired waveform characteristic on the display unit.

36. The programmer of claim 35, wherein the control unit comprises means for generating at least one cursor on the display unit that may be positioned by the user by entering instructions via the user interface, the cursor defining the specific portion of the intracardiac electrogram waveform to be analyzed as being the portion of the intracardiac electrogram waveform immediately adjacent to the cursor.

37. The programmer of claim 36, wherein the control unit further comprises means for calculating the intracardiac electrogram waveform relative amplitude within the specific portion of the intracardiac electrogram waveform to be analyzed.

38. The programmer of claim 36, wherein the control unit further comprises means for calculating the maximum slew rate of the intracardiac electrogram waveform within the specific portion of the intracardiac electrogram waveform to be analyzed.

39. The programmer of claim 36, wherein the control unit further comprises means for calculating the power spectral density of the intracardiac electrogram waveform within the specific portion of the intracardiac electrogram waveform to be analyzed.

40. The programmer of claim 35, wherein the control unit comprises means for generating at least two cursors on the display unit that may be positioned by the user by entering instructions via the user interface, the cursors defining the specific portion of the intracardiac electrogram waveform to be analyzed as being the portion of the intracardiac electrogram waveform between the cursors.

41. The programmer of claim 40, wherein the control unit further comprises means for calculating the intracardiac electrogram waveform relative amplitude within the specific portion of the intracardiac electrogram waveform to be analyzed.

42. The programmer of claim 40, wherein the control unit further comprises means for calculating the maximum slew rate of the intracardiac electrogram waveform within the specific portion of the intracardiac electrogram waveform to be analyzed.

43. The programmer of claim 40, wherein the control unit further comprises means for calculating the power spectral density of the intracardiac electrogram waveform within the specific portion of the intracardiac electrogram waveform to be analyzed.

44. The programmer of claim 40, wherein the two cursors define an elapsed time to be measured by the control unit.

45. The programmer of claim 35, wherein the control unit comprises means for generating icons on the display unit that may be positioned by the user to define the specific portion of the intracardiac electrogram waveform to be analyzed.

46. The programmer of claim 45, wherein the control unit further comprises means for calculating the intracardiac electrogram waveform relative amplitude within the specific portion of the intracardiac electrogram waveform to be analyzed.

47. The programmer of claim 45, wherein the control unit further comprises means for calculating the maximum slew rate of the intracardiac electrogram waveform within the specific portion of the intracardiac electrogram waveform to be analyzed.

48. The programmer of claim 45, wherein the control unit further comprises means for calculating the power spectral density of the intracardiac electrogram waveform within the specific portion of the intracardiac electrogram waveform to be analyzed.

49. The programmer of claim 35, further comprising means for comparing the desired waveform characteristic for the specific portion of the intracardiac electrogram waveform to statistical waveform data.

* * * * *